US009517167B2

(12) United States Patent  (10) Patent No.: US 9,517,167 B2
Sakaguchi  (45) Date of Patent: Dec. 13, 2016

(54) DISPOSABLE DIAPER WITH CUSHIONING UNIT ADJACENT A LEG STRETCH UNIT IN THE LONGITUDINAL DIRECTION

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 42 days.

(21) Appl. No.: 14/377,158

(22) PCT Filed: Feb. 4, 2013

(86) PCT No.: PCT/JP2013/052444
§ 371 (c)(1),
(2) Date: Aug. 6, 2014

(87) PCT Pub. No.: WO2013/118667
PCT Pub. Date: Aug. 15, 2013

(65) Prior Publication Data
US 2014/0358109 A1  Dec. 4, 2014

(30) Foreign Application Priority Data
Feb. 7, 2012  (JP) ................................. 2012-024546

(51) Int. Cl.
*A61F 13/49*  (2006.01)
*A61F 13/494*  (2006.01)
*A61F 13/56*  (2006.01)

(52) U.S. Cl.
CPC ... *A61F 13/49009* (2013.01); *A61F 13/49014* (2013.01); *A61F 13/49015* (2013.01);
(Continued)

(58) Field of Classification Search
CPC ................ A61F 13/15593; A61F 13/49009; A61F 13/49017; A61F 13/4902; A61F 2013/49022; A61F 2013/49036
See application file for complete search history.

(56) References Cited

U.S. PATENT DOCUMENTS 4,050,462 A * 9/1977 Woon ................ A61F 13/49017
604/365
4,300,967 A * 11/1981 Sigl .................. A61F 13/15593
156/164
(Continued)

FOREIGN PATENT DOCUMENTS

EP  0692231 A1  1/1996
JP  10-502550 A  3/1998
(Continued)

OTHER PUBLICATIONS

International Search Report mailed Mar. 12, 2013 in International Application No. PCT/JP2013/052444, filed Feb. 4, 2013.
(Continued)

*Primary Examiner* — Lynne Anderson
*Assistant Examiner* — Kathryn E. Ditmer
(74) *Attorney, Agent, or Firm* — Hauptman Ham, LLP (57) ABSTRACT

A disposable diaper includes: a pair of leg stretch units formed along a leg hole openings and being stretchable in at least a product longitudinal direction; and a cushioning unit provided adjacent to each of ends of the leg stretch units in the product longitudinal direction. Each of the leg stretch units is configured from a stretchable sheet member. A ratio of expansion and contraction of each of the cushioning units is lower than a ratio of expansion and contraction of the leg stretch units. At least a part of each of the cushioning units has a dimension in a product widthwise direction greater than a width of the leg stretch units in the product widthwise direction.

15 Claims, 6 Drawing Sheets

(52) U.S. Cl.
CPC .. *A61F 13/49017* (2013.01); *A61F 13/49413* (2013.01); *A61F 13/5633* (2013.01); *A61F 2013/49022* (2013.01); *A61F 2013/49036* (2013.01); *A61F 2013/49041* (2013.01); *A61F 2013/49092* (2013.01); *A61F 2013/49098* (2013.01)

(56) References Cited

U.S. PATENT DOCUMENTS

| | | | | |
|---|---|---|---|---|
| 4,425,127 | A * | 1/1984 | Suzuki | A61F 5/4401 604/366 |
| 4,437,860 | A * | 3/1984 | Sigl | A61F 13/49019 604/385.29 |
| 4,450,026 | A * | 5/1984 | Pieniak | A61F 13/49009 156/164 |
| 4,695,278 | A * | 9/1987 | Lawson | A61F 13/49017 604/385.24 |
| 4,850,989 | A * | 7/1989 | Villez | A61F 13/15593 604/358 |
| 4,938,821 | A * | 7/1990 | Soderlund | A61F 13/15593 156/163 |
| 5,236,430 | A * | 8/1993 | Bridges | B29C 66/4722 2/400 |
| 5,368,584 | A * | 11/1994 | Clear | A61F 13/49009 604/358 |
| H1420 | H * | 2/1995 | Richardson | A61F 13/15593 604/358 |
| 5,868,725 | A * | 2/1999 | Coles | A61F 13/15203 604/369 |
| 6,827,806 | B2 * | 12/2004 | Uitenbroek | A61F 13/15593 156/160 |

FOREIGN PATENT DOCUMENTS

| | | |
|---|---|---|
| JP | 2003-70840 A | 3/2003 |
| JP | 2004-275558 A | 10/2004 |
| JP | 2006-102278 A | 4/2006 |
| WO | 96/29038 A1 | 9/1996 |
| WO | 2010/016785 A1 | 2/2010 |

OTHER PUBLICATIONS

Office Action mailed Oct. 27, 2015, corresponding to Japanese Patent Application No. 2012-024546.

Extended European Search Report dated Sep. 9, 2015, corresponding to European Patent Application No. 13746474.9.

* cited by examiner

DISPOSABLE DIAPER WITH CUSHIONING UNIT ADJACENT A LEG STRETCH UNIT IN THE LONGITUDINAL DIRECTION

RELATED APPLICATIONS

The present application is a National Phase of International Application Number PCT/JP2013/052444 filed Feb. 4, 2013, which claims priority to Japanese Application No. 2012-024546 filed Feb. 7, 2012.

TECHNICAL FIELD

The present invention relates to a disposable diaper.

BACKGROUND ART

Conventionally, there is known an open-type disposable diaper which has a front waistline region, a back waistline region, a crotch region, a pair of leg hole openings, an absorber spanning the crotch region and extending to the front waistline region and back waistline region, and a fastening tape provided in the back waistline region.

In the above open-type disposable diaper, there has been known a structure in which a skin contact surface side of a proximal end of the fastening tape is covered by side flaps (nonwoven fabric) more flexible than the fastening tape (for example, see Patent Literature 1).

According to the above structure, it is possible to reduce the stimulation on the skin of the wearer by the proximal end of the fastening tape, and thus it is less likely that the wearer obtains a feeling of discomfort and pain at the time of wearing the open-type disposable diaper.

CITATION LIST

Patent Literature

[PTL 1]
Japanese Unexamined Patent Application Publication No. 2003-70840

SUMMARY OF INVENTION

However, the applicant discovered that when the open-type disposable diaper was worn, a region between the proximal end of the fastening tape at the skin contact surface side and the leg stretch unit formed along the leg hole openings was most likely to exert the stimulation on the wearer.

Thus, the present invention has been achieved in view of the above problem, and an object thereof is to provide a disposable diaper with which it is possible to reduce the stimulation exerted by the region between the proximal end of the fastening tape at the skin contact surface side and the leg stretch unit formed along the leg hole openings on the skin of the wearer.

A first characteristic of the present invention is summarized as a disposable diaper having a front waistline region; a back waistline region; a crotch region positioned between the front waistline region and the back waistline region; a pair of leg hole openings; an absorber spanning the crotch region and extending to the front waistline region and back waistline region; a product longitudinal direction from the front waistline region towards the back waistline region; and a product widthwise direction perpendicular to the product longitudinal direction; wherein the disposable diaper further includes: a pair of leg stretch units formed along the leg hole openings and being stretchable in at least the product longitudinal direction; and a cushioning unit provided in the region adjacent to the ends of the leg stretch units in the product longitudinal direction; the leg stretch units are configured from a stretchable sheet member; the ratio of expansion and contraction of the cushioning unit is configured to be lower than the ratio of expansion and contraction of the leg stretch units; and a width of at least a part of the cushioning unit in the product widthwise direction is configured to be longer than a width of the leg stretch units in the product widthwise direction.

DESCRIPTION OF EMBODIMENTS

First Embodiment of the Present Invention

With reference to FIG. 1 through FIG. 7B, a disposable diaper 10 according to a first embodiment of the present invention will be described.

In the following description of the drawings, the same or similar reference numerals are used to designate the same or similar portions. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

Figure 1:
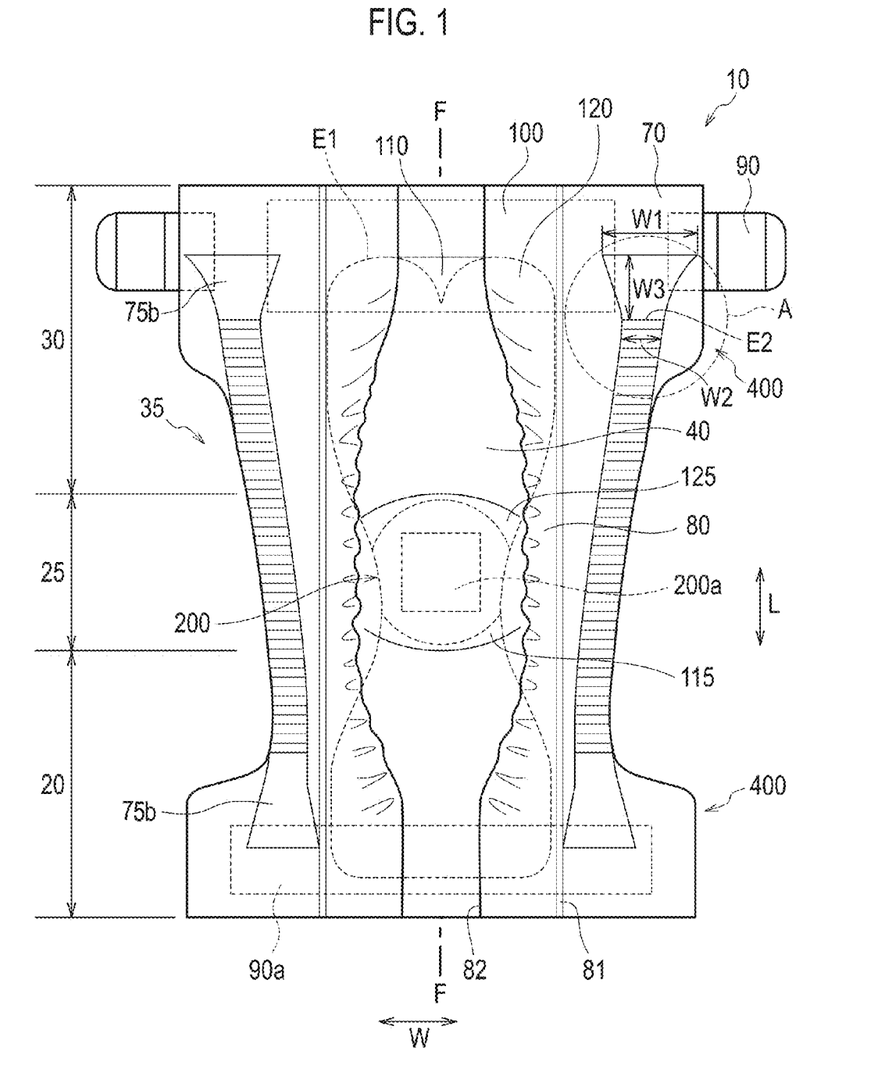
FIG. 1 is a plan view of an open-type disposable diaper according to a first embodiment of the present invention.
Figure 2:
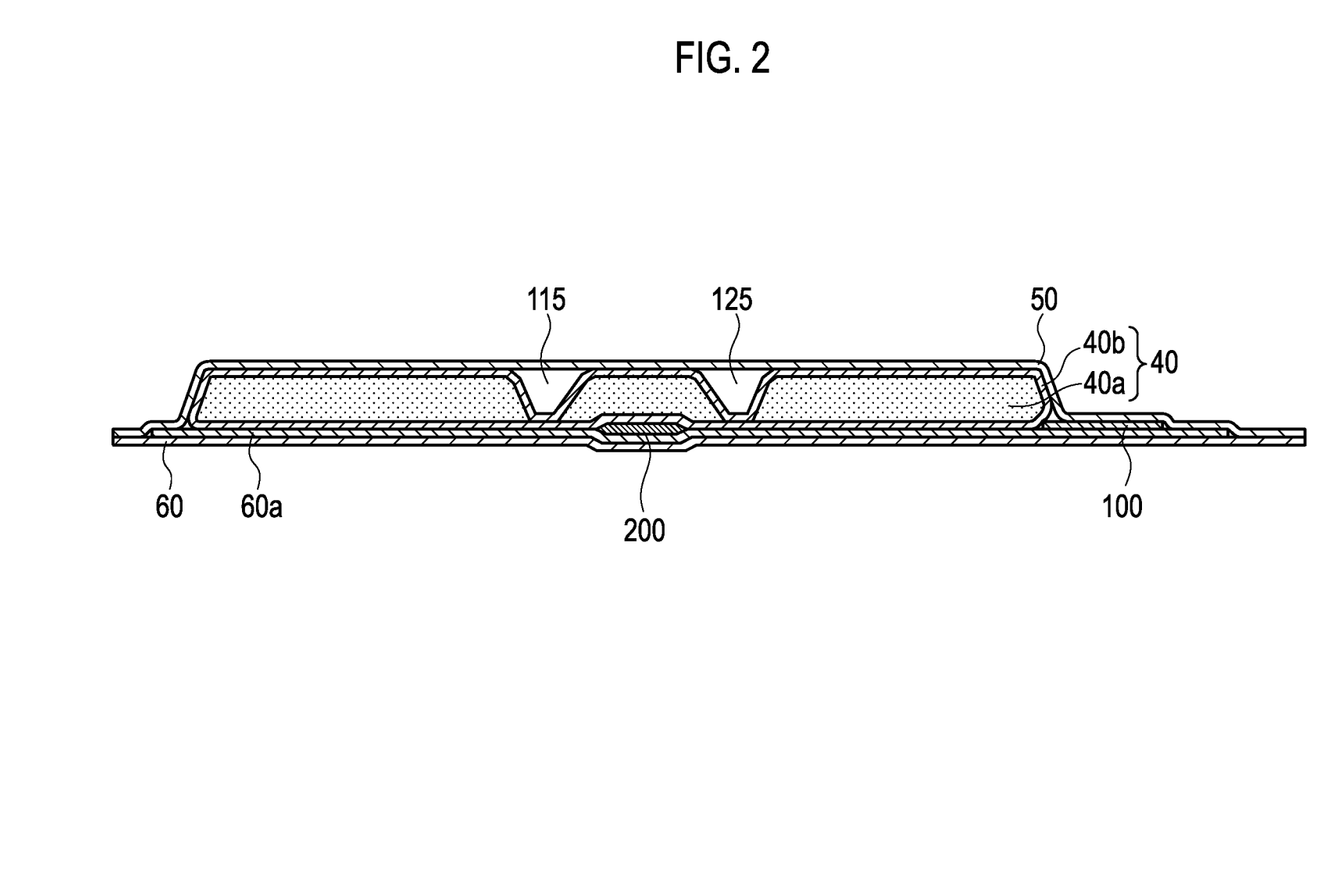
FIG. 2 is a diagram of an F-F cross section in the plan view of the open-type disposable diaper according to the first embodiment of the present invention.

FIG. 1 is a plan view of the disposable diaper 10 according to the present embodiment. FIG. 2 is a cross-sectional view of the open-type disposable diaper 10 along the F-F line illustrated in FIG. 1. It must be noted that the plan view of FIG. 1 is a diagram in which leg gathers 75 and leg side gathers 80 are in an elongated state such that wrinkles are not formed in a topsheet 50 and side sheets 70 that configure the disposable diaper, but for the sake of description, the leg side gathers 80 are illustrated in a stretched state.

As illustrated in FIG. 1, the disposable diaper 10 includes a front waistline region 20, a crotch region 25, and a back waistline region 30. Furthermore, a pair of leg hole openings are formed in the open-type disposable diaper 10.

Here, the front waistline region 20 is the portion that is in contact with the front waistline portion of the wearer, the back waistline region 30 is the portion that is in contact with a back waistline portion of the wearer, and the crotch region 25 is the portion positioned between the front waistline region 20 and the back waistline region 30.

In the present embodiment, the direction from the front waistline region 20 towards the back waistline region 30 is called the product longitudinal direction L, and the direction perpendicular to the product longitudinal direction L is called the product widthwise direction W.

The disposable diaper 10 includes an absorber 40 spanning the crotch region 25 and extending in the front waistline region 20 and the back waistline region 30. As illustrated in FIG. 2, the absorber 40 is configured from an absorber core 40a and a core wrap 40b.

The absorber core 40a is same as in the conventional disposable diaper, and can be configured appropriately by using popular components and materials, such as ground pulp and high absorbent polymer. The absorber core 40a is wrapped by the sheet-like core wrap 40b.

The core wrap 40b is a sheet for wrapping the absorber core 40a. A part of at least the skin surface contact side of the core wrap 40b is configured by various fibrous nonwoven fabrics or a tissue sheet having liquid-permeability.

For example, an air-through fibrous nonwoven fabric, a spunbond nonwoven fabric, or an SMS (spunbond-meltblown-spunbond) nonwoven cloth having a mass of approximately 10 to 30 $g/m^2$, or a tissue sheet having a mass of approximately 10 to 30 $g/m^2$ can be used as the component configuring the core wrap 40b.

Figure 3:
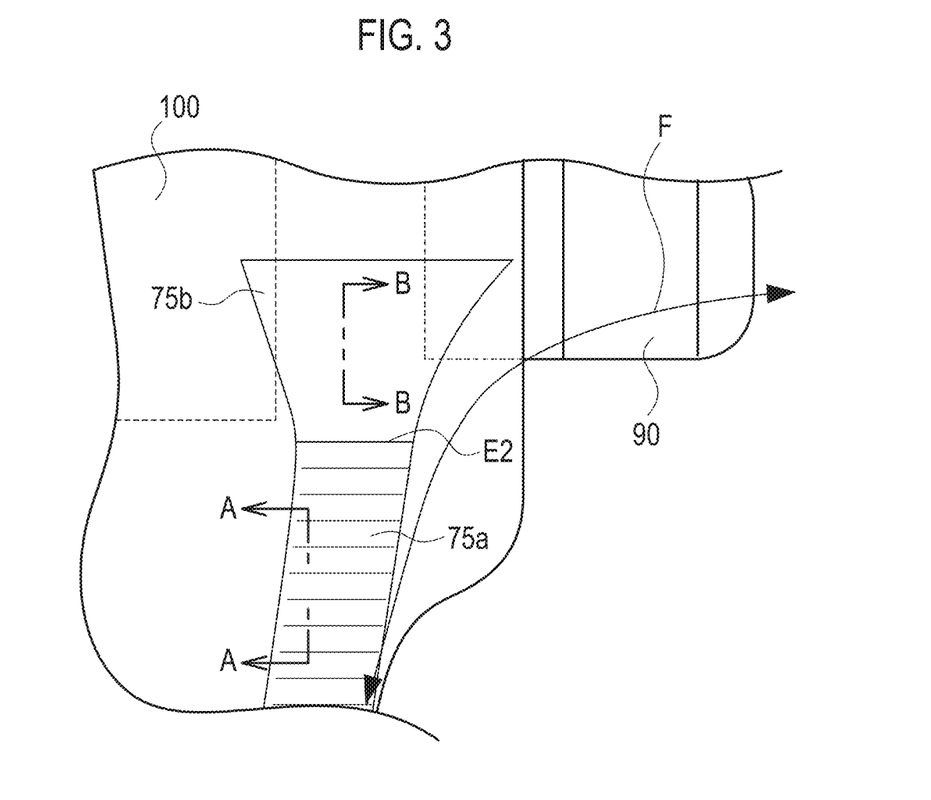
FIG. 3 is an enlarged view of a region A in the plan view of the open-type disposable diaper according to an embodiment of the present invention.

Furthermore, as illustrated in FIG. 3, the liquid-permeable topsheet 50 is provided at the top side (skin contact surface side) of the absorber 40, and a liquid-impermeable backsheet 60 is provided at the back side (non-skin contact surface side) of the absorber 40. A side flap 70 is provided at each side edge in the product widthwise direction W of the absorber 40. The side flaps 70 are made of one or two or more pieces of nonwoven fabrics overlapping one another.

Furthermore, the disposable diaper 10 includes a pair of fastening tapes 90 in the back waistline region 30, and includes a target tape 90a in a predetermined region of the non-skin contact surface side of the front waistline region 20.

Here, by mounting the fastening tape 90 on the target tape 90a, the disposable diaper 10 can be retained on the body of the wearer.

In the present embodiment, the front waistline region 20, the back waistline region 30, and the fastening tape 90 configure the waistline retaining unit 400 configured to retain the disposable diaper 10 on the body of the wearer. Here, the waistline retaining unit 400 extends along the product widthwise direction W.

Furthermore, the disposable diaper 10 may include a crotch stretch unit 200a formed in the crotch region 25 and being stretchable in the product longitudinal direction L.

Specifically, the crotch stretch unit 200a may be arranged in a crotch unit 200 formed in the crotch region 25.

Furthermore, the center of the crotch stretch unit 200a in the product longitudinal direction L is arranged at the side of the front waistline region 20 from the center of the disposable diaper 10 in the product longitudinal direction L. However, the crotch stretch unit 200a is arranged to span the center of the disposable diaper 10 in the product longitudinal direction L.

In the present embodiment, the crotch stretch unit 200a may be configured from a stretchable sheet.

For example, a stretch film formed by melting a thermoplastic elastomer resin, such as urethane and styrene, and then converting into the shape of a film, a stretchable nonwoven fabric formed from such stretchable fibers, or a composite sheet formed by pasting together inextensible sheets that have been partially cut into a stretchable film and stretchable nonwoven fabric, or have been made fragile can be used as the stretchable sheet.

Furthermore, rather than the stretchable sheet, the crotch stretch unit 200a may also be configured through an alternate, parallel arrangement of thread-like or stripe-like stretchable elastic members made from polyurethane elastic fibers and natural rubber.

In such a case, in view of the rigidity of the absorber core 40a and the rigidity of other members configuring the open-type disposable diaper 10, the thickness of the elastic members and the arrangement pitch can be selected appropriately, however, when the main body of the open-type disposable diaper 10 is in the natural state (unextended state), the entire side edge in the product widthwise direction W of the absorber core 40a is preferable to be in a contracted state.

Specifically, the ratio of expansion and contraction of the crotch stretch unit 200a is preferably 1.2 times to 1.8 times. For example, in the present embodiment, the ratio of expansion and contraction of the crotch stretch unit 200a may be set to 1.4 times.

The ratio of expansion and contraction implies the extent of expansion and contraction of the crotch stretch unit 200a in the stretching direction (product longitudinal direction L in the present embodiment), and is stipulated as below:

Ratio of expansion and contraction=(Length in the stretching direction of the crotch stretch unit 200a in the maximum extended state)/(Length in the stretching direction of the crotch stretch unit 200a in the natural state)

It should be noted that the ratio of expansion and contraction as used herein is to be measured as described below, for example.

Firstly, if the disposable diaper 10 is inserted in a package, for example, then the open-type disposable diaper 10 is taken out of the package, and the diaper is kept in such a condition for 60 minutes in an ambient atmosphere having a temperature of 20° C.±2° C., and a relative humidity of 60%±5% RH.

Secondly, the length in the stretching direction of the desired region of the open-type disposable diaper in this state (that is, in the natural state), and the length in the stretching direction of the desired region, when the open-type disposable diaper is extended from its natural state until wrinkles caused by the elastic members are not visible, are measured.

By thus setting the ratio of expansion and contraction of the crotch stretch unit 200a to 1.2 times to 1.8 times, it is possible to favorably follow the stretching of the skin of the wearer.

For example, when the wearer is slouchy such that the front side of the body is cringing, the skin at the side of the hip portion of the wearer stretches by approximately 30% as compared to the state when the body has been stretched out That is, when the ratio of expansion and contraction of the crotch stretch unit 200a is 1.2 times or less, the contraction of the crotch stretch unit 200a in the natural state of the open-type disposable diaper is insufficient, and as compared to the case when the crotch stretch unit 200a has not been provided, the difference in the ease of curving of the disposable diaper 10 is small because of which the front waistline region 20 does not rise at the desired position.

On the other hand, when the ratio of expansion and contraction of the crotch stretch unit 200a is more than 1.8 times, the contraction size in the contraction direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the disposable diaper 10 may include a waist stretch unit (waist gathers) 100 formed in the back waistline region 30 and stretchable in the product widthwise direction W.

In the present embodiment, similarly to the crotch stretch unit 200a, the waist stretch unit 100 may be configured from a stretchable sheet member. The member configuring the waist stretch unit 100 is not particularly restricted, but a member that is as thin as possible with a low rigidity, and has a small reduction in width is preferably used.

In the present embodiment, a stretch film having a basis weight of 30 g/m$^2$ is used as the waist stretch unit 100. The stretch film is preferably used from the viewpoint of reducing the basis weight After being extended up to 1.5 to 2.5 times the length in the non-elongated state (natural state), the waist stretch unit 100 is adhered onto the backsheet 60 with a hot-melt adhesive or heat processing.

The waist stretch unit 100 is arranged between the topsheet 50 and the backsheet 60. As illustrated in FIG. 2, the core wrap 40b is arranged between the topsheet 50 and the waist stretch unit 100.

Alternatively, when an exterior sheet 60a arranged between the absorber 40 and the backsheet 60 has been provided, the waist stretch unit 100 may be arranged between the exterior sheet 60a and the backsheet 60.

Furthermore, when a leakage-preventing sheet is arranged intermittently in the product longitudinal direction L, the waist stretch unit 100 may perform the role of a leakage-preventing member. In such a case, the width of the waist stretch unit 100 is preferably more than the width of the absorber 40.

Furthermore, the waist stretch unit 100 may be configured such that when the waist stretch unit 100 is contracted in the product widthwise direction W, the width reduction rate in the product longitudinal direction L becomes 30% or less.

By setting the width reduction rate of the waist stretch unit 100 to 30% or less, and preferably to 10% or less, the contraction of the waist stretch unit 100 in the product longitudinal direction L is controlled, and even when the waist stretch unit 100 is arranged in the hip portion, the shifting of the ends of the back waistline region 30 from the predetermined position due to the contraction of the product longitudinal direction L can be controlled.

It should be note that the width reduction rate as used herein is to be measured as described below, for example.

Firstly, the waist stretch unit 100 is taken out from the open-type disposable diaper 10, the waist stretch unit 100 that has been taken out is kept in an ambient atmosphere having a temperature of 20° C.±2° C., and a relative humidity of 60%±5% RH for 24 hours, and then the width of the position corresponding to the center in the product widthwise direction W during the arrangement of the waist stretch unit 100 in the open-type disposable diaper 10 is set to the sheet-like elastic element width (WA) in the natural state.

Secondly, the entire width of the waist stretch unit 100 that has been taken out is held between the measuring chuck of the tensile testing machine (Autograph manufactured by Shimadzu Corporation), elongated the waist stretch unit 100 up to the width at the time of pasting to the open-type disposable diaper 10 at a speed of 100 mm/min, and then the width (WB) at the position corresponding to the center in the product widthwise direction W of the waist stretch unit 100 during the arrangement in the open-type disposable diaper 10 is measured.

Now, the measured (WA) and (WB) are used to calculate the width reduction rate with the expression described below.

$$\text{Width reduction rate (\%)}=((WA)-(WB))/(WA))\times 100$$

The absorber 40 may include low rigidity regions 115 and 125, where the basis weight is low or the absorber core 40a does not exist, along the ends in the product longitudinal direction L of the front waistline region 20 and the back waistline region 30 in the crotch stretch unit 200a, that is, along the edges in the product longitudinal direction L of the crotch unit 200.

Furthermore, the absorber 40 may include a low rigidity region 110, where the basis weight is lower than the other parts of the absorber 40 or the absorber core 40a does not exist, in the back waistline region 30. Furthermore, the low rigidity region 110 may be formed to extend up to the proximity of the end E1 at the back waistline region 30 side in the product longitudinal direction L of the absorber 40.

The width of the low rigidity region 110 in the product widthwise direction W widens towards the ends at the back waistline region 30 side in the product longitudinal direction L More specifically, the low rigidity region 110 has a wedge shape in the plan view of the disposable diaper 10.

Additionally, the absorber 40 may include a stretch control region 120, which is the region where the stretch in the product widthwise direction W is more controlled than that in the other regions.

Here, as illustrated in FIG. 1, the stretch control region 120 may be formed at each of the outer sides in the product widthwise direction W of the low rigidity region 110.

Furthermore, the boundary between the stretch control region 120 and the low rigidity region 110 may be formed in the shape of an arc such as a convex shape towards the center in the product widthwise direction W.

It must be noted that the waist stretch unit 100 and the absorber 40 may be configured to overlap in at least one part in the plan view of the disposable diaper 10. Specifically, the waist stretch unit 100 may be configured to overlap at least a part of the low rigidity region 110, in the plan view of the disposable diaper 10.

The top side (topsheet 50 side) of the absorber 40 includes a pair of leg stretch units (leg gathers) 75a formed along the leg hole openings 35 and stretchable in at least the product longitudinal direction L.

The leg stretch unit 75a is configured to be longer than the crotch stretch unit 200a in the product longitudinal direction L, and is provided at the outer side from the crotch stretch unit 200a in the product widthwise direction W.

Furthermore, similarly to the crotch stretch unit 200a and the waist stretch unit 100, the leg stretch unit 75a may be formed from a stretchable sheet member.

Specifically, the width (the width in the product widthwise direction W in the natural state of the disposable diaper 10) of the stretchable sheet member is preferably 5 mm or more and 35 mm or less, in at least the crotch region 25.

Here, when the width of the stretchable sheet member is less than 5 mm, the effect arising from the stretchable sheet member substantially planarly running along the leg holes of the wearer is not achieved, and when the width of the stretchable sheet member exceeds 35 mm, the region running along the leg holes widens, and the stretchable sheet member may easily is pulled in towards the body of the wearer or may easily fold over.

The ratio of expansion and contraction of the leg stretch units 75a preferably is 1.5 to 2.4 times. For example, in the present embodiment, the ratio of expansion and contraction of the leg stretch units 75a may be set to 1.9 times. The ratio of expansion and contraction of the leg stretch units 75a is stipulated in the same manner as the ratio of expansion and contraction of the aforementioned crotch stretch unit 200a.

Furthermore, the interval between the inner ends in the product widthwise direction W of the pair of the left-right leg stretch units 75a widens from the crotch region 25 towards the front waistline region 20, and also widens from the crotch region 25 towards the back waistline region 30.

The interval is obtained by measuring the distance between the inner ends in the product widthwise direction W of the pair of the left-right leg stretch units 75a, after the disposable diaper 10 is stretched in the product longitudinal direction L and the product widthwise direction W from the natural state until the state when wrinkles are not visible visually, and retained in that state.

Furthermore, a pair of leg side gathers 80 extending along the product longitudinal direction L may be provided at the inner side of the pair of leg stretch units 75a (towards the center of the product widthwise direction W).

The leg side gathers 80 include a joining portion 81, and a free end portion 82 positioned at the opposite side of the joining portion 81 and provided with an elastic member (not illustrated in the figure).

Here, the joining portion 81 may be joined with the topsheet 50, or may be joined with the leakage-preventing film or backsheet 60 arranged at the non-skin contact surface side from the topsheet 50.

Furthermore, the ends in the product longitudinal direction L of the free end portion 82 are joined with the topsheet 50. The joining portion 81 is arranged between the crotch stretch unit 200a and the leg stretch unit 75a, in the product widthwise direction W.

As for the leg side gathers 80, when the diaper is worn, the joining portion 81 rises up as the proximal end and the free end portion 82 is in contact with the skin of the wearer as the apex.

In the present embodiment, as illustrated in FIG. 3, the disposable diaper 10 includes a cushioning unit 75b provided in the region adjacent to the end E2 of the leg stretch units 75a in the product longitudinal direction L.

For example, the leg stretch units 75a and the cushioning unit 75b may be configured from the same stretchable sheet member.

Figure 4:
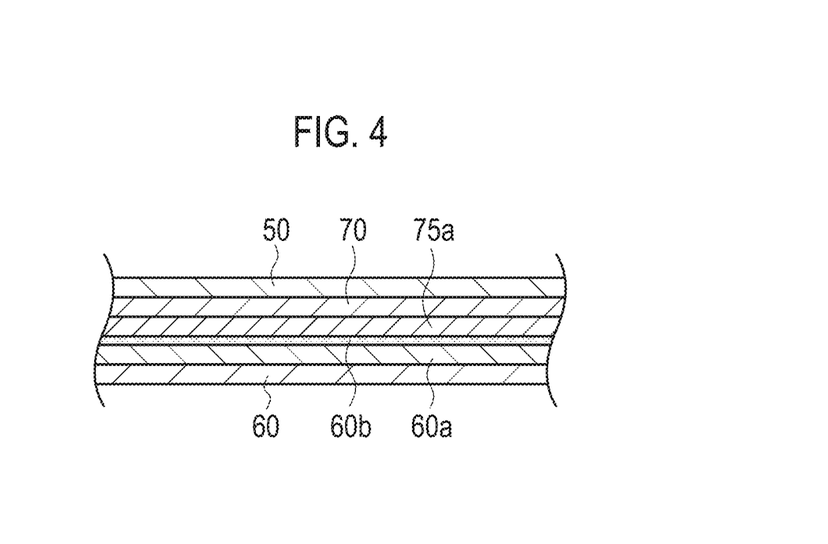
FIG. 4 is a diagram of an A-A cross section in the enlarged view of the region A in the plan view of the open-type disposable diaper according to the first embodiment of the present invention.
Figure 5:
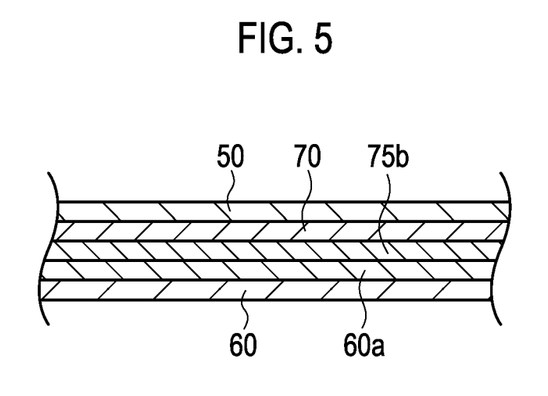
FIG. 5 is a diagram of a B-B cross section in the enlarged view of the region A in the plan view of the open-type disposable diaper according to the first embodiment of the present invention.

As illustrated in FIG. 4, the leg stretch units 75a are configured from a region in which an adhesive 60b is applied in the stretchable sheet member, and as illustrated in FIG. 5, the cushioning unit 75b may be configured from a region in which an adhesive 60b is not applied in the stretchable sheet member.

Specifically, as illustrated in FIG. 4 and FIG. 5, the leg stretch units 75a and the cushioning unit 75b are arranged between the exterior sheet (back film) 60a and the side flaps 70. It must be noted that when the exterior sheet 60a is not provided, the leg stretch units 75a and the cushioning unit 75b are arranged between the backsheet 60 and the side flaps 70.

In such a case, because there is no need to prepare and arrange a member different from the member configuring the leg stretch units 75a, the manufacturing method can be simplified.

Furthermore, the ratio of expansion and contraction of the cushioning unit 75b is configured to be lower than the ratio of expansion and contraction of the leg stretch units 75a. For example, the ratio of expansion and contraction of the cushioning unit 75b may be set to 1.0 to 1.3 times.

The ratio of expansion and contraction of the cushioning unit 75b is stipulated in the same manner as the ratio of expansion and contraction of the aforementioned crotch stretch unit 200a.

As a result, the cushioning unit 75b becomes softer as compared to the leg stretch units 75a, and because of the cushioning unit 75b, the stimulation exerted by the region between the proximal end of the fastening tape 90 at the skin contact surface side and the leg stretch unit 75a on the skin of the wearer can be alleviated.

Furthermore, the width W1 of at least a part of the cushioning unit 75b in the product widthwise direction W is configured to be greater than the width W2 of the leg stretch units 75a in the product widthwise direction W.

According to the above configuration, the cushioning unit 75b can alleviate the stimulation exerted on the skin of the wearer in a wide range along the leg hole openings 35 between the proximal end of the fastening tape 90 at the skin contact surface side and the leg stretch unit 75a.

For example, the length W3 of the cushioning unit 75b in the product longitudinal direction L may be configured to be 10 to 15 mm Furthermore, the cushioning unit 75b may be provided to cross the waistline retaining unit 400.

Here, when the disposable diaper 10 is worn, the region in proximity of the sides of the waistline retaining unit 400 (the joining unit of the front waistline region 20 and the back waistline region 30) corresponds to the part close to the sides, from the buttocks of the wearer up to the dorsal area.

The part close to the sides is the part where the ratio of expansion and contraction of the surface of the skin is relatively large due to the movement of the wearer. For example, when the wearer moves from a state in which the body is stretched out to a state in which the body is curled, the surface of the skin in that part stretches by about 20 to 30%, and therefore, the part may receive a high pressure due to the movement of the wearer.

As described above, when the cushioning unit 75b and the waistline retaining unit 400 cross each other, the part close to the sides can be protected firmly.

Additionally, the cushioning unit 75b may be configured to cross the region in which the fastening tape 90 is provided, and the region in which the target tape 90a is provided.

Here, because the region in which the fastening tape 90 is provided and the region in which the target tape 90a is provided to retain the disposable diaper 10 on the waistline of the wearer when the disposable diaper 10 is worn, a force is generated along the waistline direction of the wearer, and because of this force, a pressure is applied to the skin of the wearer.

Therefore, as described above, when the cushioning unit 75b crosses the region in which the fastening tape 90 is provided and the region in which the target tape 90a is provided, the part of the wearer body corresponding to the region in which the fastening tape 90 is provided and the region in which the target tape 90a is provided can be protected firmly.

Furthermore, the width of the cushioning unit 75b in the product widthwise direction W may be configured to become greater towards the ends in the product longitudinal direction L.

Specifically, as illustrated in FIG. 3, the side edges at the outer side in the product widthwise direction W of the cushioning unit 75b may be configured to run along a line F which is along the leg holes of the disposable diaper 10 (that is, the line connecting the end E2 of the leg stretch units 75a in the product longitudinal direction L and the proximal end 90A of the fastening tape 90).

As a result of the experiment, the present applicant discovered that a pressure was most likely to be exerted on the wearer in the region that cannot be stretched (particularly, the region towards the leg stretch units 75a) on the aforementioned line F, at the time of wearing the disposable diaper 10.

Therefore, by configuring the side edges at the outer side in the product widthwise direction W of the cushioning unit 75b as described above, it is possible to protect, by using the cushioning unit 75b, the region in which the pressure is most likely to be exerted on the wearer.

Furthermore, in the natural state, the cushioning unit 75b may be configured to be thicker than the region in which the fastening tape 90 is fixed.

As a result, the stimulation exerted by the region in which the fastening tape 90 is fixed on the skin of the wearer can be alleviated by providing the cushioning unit 75b.

Next, an example of an operation of generating the leg stretch units 75a and the cushioning unit 75b of the disposable diaper 10 according to the present embodiment is explained with reference to FIG. 6 through FIG. 8.

Firstly, a first operation example for generating the leg stretch units 75a and the cushioning unit 75b of the disposable diaper 10 according to the present embodiment is explained with reference to FIG. 6 and FIG. 7.

Figure 6:
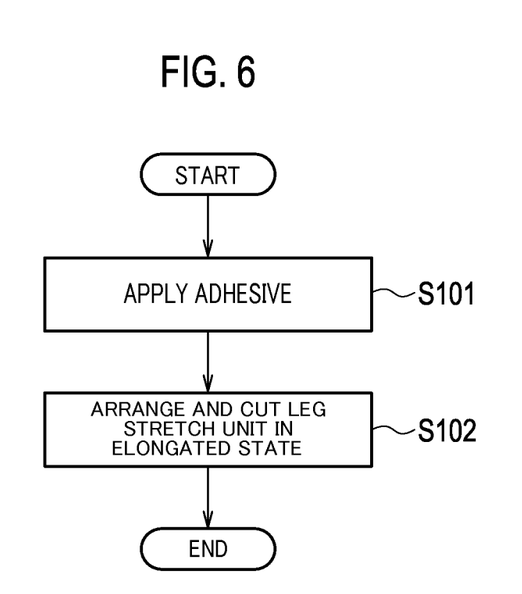
FIG. 6 is a flowchart illustrating an operation of generating a leg stretch unit and a cushioning unit of the open-type disposable diaper according to the first embodiment of the present invention.

As illustrated in FIG. 6, in step S101, in a predetermined region of a continuous body of the exterior sheet 60a that is being conveyed, that is, in the region in which the leg stretch units 75a are formed, an adhesive is applied (the adhesive is not applied in the region in which the cushioning unit 75b is formed).

In step S102, a member 75 in an extended state is arranged on the exterior sheet 60a, and is cut at the end position of the product longitudinal direction L in the product.

As a result, the member 75 in the region where the adhesive is not applied on the exterior sheet 60a is not retained in the exterior sheet 60a and gets contracted due to which the member is released from the extended state, and the cushioning unit 75b is formed.

Figure 7A:
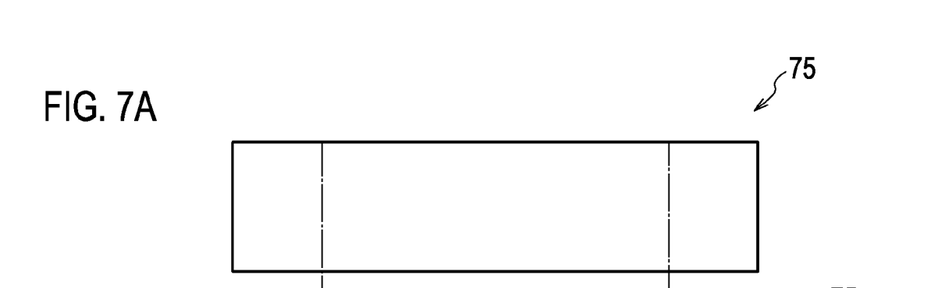
FIGS. 7A and 7B each is a diagram for explaining an operation of generating a leg stretch unit and a cushioning unit of the open-type disposable diaper according to the first embodiment of the present invention.
Figure 7B:
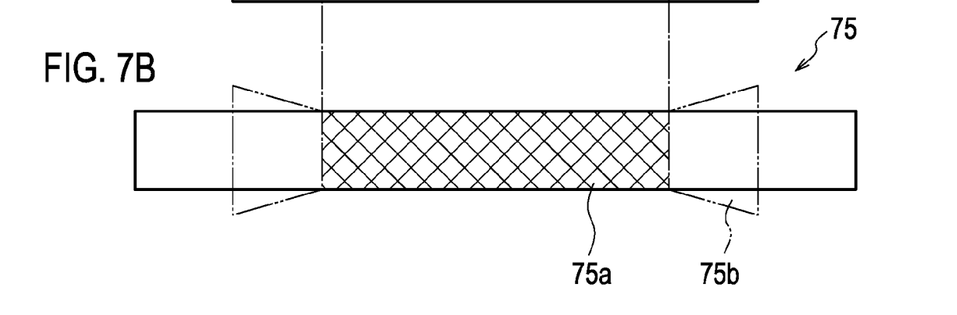

For example, in step S102, as illustrated in FIG. 7(b), the member 75 in the natural state illustrated in FIG. 7(a) is pulled in the MD direction, and upon transit to the extended state, the member 75 is cut and then arranged in a predetermined region of a continuous body of the exterior sheet 60a.

As a result, as illustrated in FIG. 7(b), the leg stretch units 75a are transferred and retained in a predetermined region of a continuous body of the exterior sheet 60a in the stretching state itself.

On the other hand, because an adhesive is not applied in the predetermined region in which the cushioning unit 75b is arranged, the cushioning unit 75b tries to return to the natural state, as illustrated in FIG. 7(b), resulting in a shape where the width of the cushioning unit 75b in the product widthwise direction W becomes greater towards the opposite side of the leg stretch units 75a.

Secondly, a second operation example for generating the leg stretch units 75a and the cushioning unit 75b of the disposable diaper 10 according to the present embodiment is explained with reference to FIG. 8.

Figure 8:
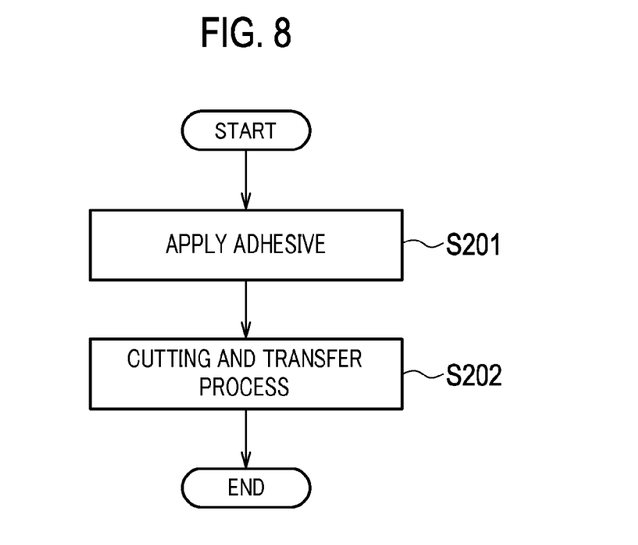
FIG. 8 is a flowchart illustrating another operation of generating a leg stretch unit and a cushioning unit of the open-type disposable diaper according to the first embodiment of the present invention.

As illustrated in FIG. 8, in step S201, an adhesive is applied in a predetermined region of a continuous body of the exterior sheet 60a being conveyed.

In step S202, through the cutting and transfer process, the member 75 in the extended state is arranged at a predetermined position of the exterior sheet 60a. Here, at the position corresponding to the region of the cushioning unit 75b in the member 75, by releasing the suction power and reducing the suction region, the cutting and transfer process can be performed in a state in which the extension of the region of the cushioning unit 75b has been relaxed.

It must be noted that according to the second operation example, by applying an adhesive in the region of the cushioning unit 75b, the ratio of expansion and contraction of the cushioning unit 75b can be maintained higher than 1.0.

According to the disposable diaper 10 of the present embodiment, as a result of the cushioning unit 75b provided in the region adjacent to the end E2 of the leg stretch units 75a in the product longitudinal direction L, it is possible to reduce the stimulation exerted by the region between the proximal end of the fastening tape 90 at the skin contact surface side and the leg stretch units 75a formed along the leg hole openings 35 on the skin of the wearer.

(First Modification)

Figure 9:
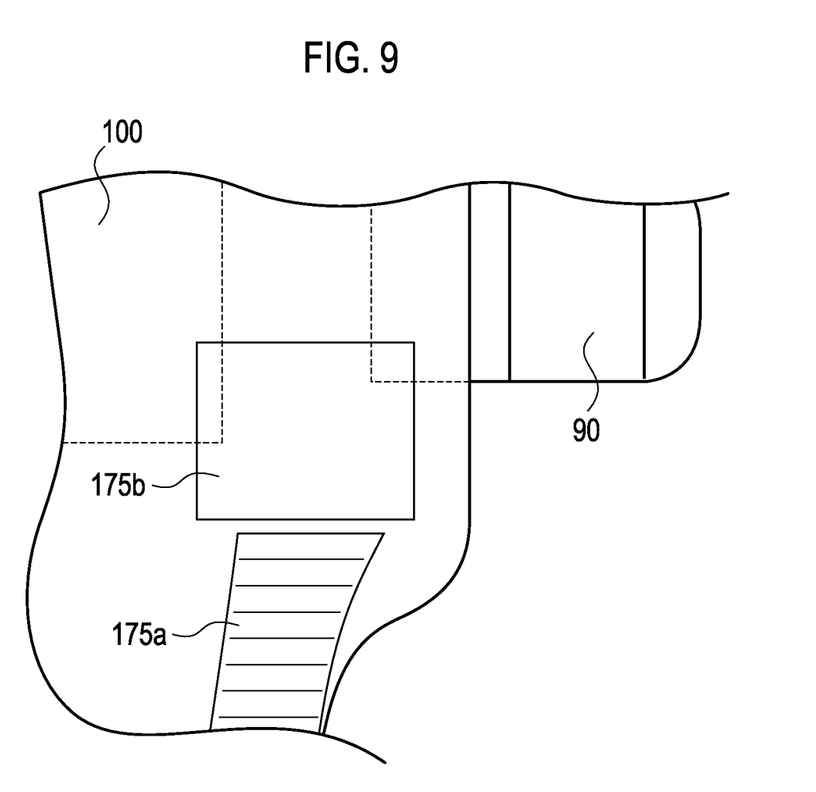
FIG. 9 is an enlarged view of the region A in the plan view of the open-type disposable diaper according to a first modification of the present invention.

With reference to FIG. 9, the disposable diaper 10 according to a first modification of the present invention will be explained. Next, only the points that are different from the disposable diaper 10 according to the first embodiment described above will be explained for the disposable diaper 10 according to the first modification of the present invention.

In the disposable diaper 10 according to the first modification of the present invention, as illustrated in FIG. 9, the leg stretch units 175a and the cushioning unit 175b may be configured from separate members.

Furthermore, the leg stretch units 175a and the cushioning unit 175b may be configured such that they are not in contact with each other.

Thus, the present invention has been explained in detail by using the above-mentioned embodiments; however, it is obvious that for persons skilled in the art, the present invention is not limited to the embodiments explained herein. The present invention can be implemented as corrected and modified modes without departing from the gist and the scope of the present invention defined by the claims. Therefore, the description of the specification is intended for explaining the example only and does not impose any limited meaning to the present invention.

In addition, the entire content of Japanese Patent Application No. 2012-024546 (filed on Feb. 7, 2012) is incorporated in the present specification by reference.

INDUSTRIAL APPLICABILITY

It is possible to provide a disposable diaper with which it is possible to reduce the stimulation exerted by the region between the proximal end of the fastening tape at the skin contact surface side and the leg stretch unit formed along the leg hole openings on the skin of the wearer.

The invention claimed is:

1. A disposable diaper, comprising:
   a front waistline region;
   a back waistline region;
   a crotch region positioned between the front waistline region and the back waistline region;
   a pair of leg hole openings;
   an absorber spanning the crotch region and extending to the front waistline region and back waistline region;
   a product longitudinal direction from the front waistline region towards the back waistline region;
   a product widthwise direction perpendicular to the product longitudinal direction;
   a pair of leg stretch units formed along the leg hole openings and being stretchable in at least the product longitudinal direction, each of the leg stretch units having a front end and a back end in the product longitudinal direction; and
   a cushioning unit provided adjacent to each of the ends of each of the leg stretch units in the product longitudinal direction, respectively,
   wherein
   each of the leg stretch units is configured from a stretchable sheet member,
   a ratio of expansion and contraction of each of the cushioning units is lower than a ratio of expansion and contraction of the respective leg stretch unit,
   at least a part of each of the cushioning units has a dimension in the product widthwise direction greater than a width of the respective leg stretch unit in the product widthwise direction,
   each of the cushioning units is provided on an outer side of the respective leg stretch unit in the product longitudinal direction, and is not provided on an inner side of the respective leg stretch unit in the product widthwise direction,
   a width of each of the cushioning units in the product widthwise direction gradually increases away from the respective leg stretch unit in the product longitudinal direction,
   each of the cushioning units has an outer end in the product longitudinal direction,
   the outer end of each of the cushioning units is provided on an inner side of an end of the front waistline region or the back waistline region in the product longitudinal direction, and
   each of the cushioning units is a region of the stretchable sheet member of the respective leg stretch unit in which an adhesive is not applied.

2. The disposable diaper according to claim 1, further comprising a front waistline retaining unit and a back waistline retaining unit extending along the product widthwise direction in the front waistline region and the back waistline region, respectively, and configured to retain the disposable diaper on a wearer's body,
   wherein each of the cushioning units overlaps the front waistline retaining unit or the back waistline retaining unit.

3. The disposable diaper according to claim 1, further comprising:
   a fastening tape provided in the back waistline region; and
   a target tape provided in the front waistline region,
   wherein
   at least one of the cushioning units overlaps either the fastening tape or the target tape in a thickness direction perpendicular to the product longitudinal direction and the product widthwise direction.

4. The disposable diaper according to claim 1, further comprising:
   a fastening tape provided in the back waistline region and having opposing inner and outer ends in the product longitudinal direction; and
   a target tape provided in the front waistline region and having opposing inner and outer ends in the product longitudinal direction.

5. The disposable diaper according to claim 4, wherein
   the outer ends of the cushioning units in the back waistline region are arranged between the outer end of the fastening tape and the inner end of the fastening tape in the product longitudinal direction, and
   the outer ends of the cushioning units in the front waistline region are arranged between the outer end of the target tape and the inner end of the target tape in the product longitudinal direction.

6. The disposable diaper according to claim 1, further comprising a sheet member,
   wherein
   each of the leg stretch units is directly attached to the sheet member by an adhesive, and
   each of the cushioning units is free of direct attachment to the sheet member by the adhesive.

7. The disposable diaper according to claim 6, wherein each of the leg stretch units is a region of the respective stretchable sheet member in which an adhesive is applied.

8. A disposable diaper, comprising:
   a front waistline region;
   a back waistline region;
   a crotch region positioned between the front waistline region and the back waistline region;
   a pair of leg hole openings;
   an absorber spanning the crotch region and extending to the front waistline region and back waistline region;
   a product longitudinal direction from the front waistline region towards the back waistline region;
   a product widthwise direction perpendicular to the product longitudinal direction;
   a pair of leg stretch units formed along the leg hole openings and being stretchable in at least the product longitudinal direction, each of the leg stretch units having a front end and a back end in the product longitudinal direction; and
   a cushioning unit provided adjacent to each of the ends of each of the leg stretch units in the product longitudinal direction, respectively,
   wherein
   each of the leg stretch units is configured from a stretchable sheet member,
   at least a part of each of the cushioning units has a dimension in the product widthwise direction greater than a width of the respective leg stretch unit in the product widthwise direction,
   each of the cushioning units is provided on an outer side of the respective leg stretch unit in the product longitudinal direction, and is not provided on an inner side of the respective leg stretch unit in the product widthwise direction, a width of each of the cushioning units in the product widthwise direction gradually increases away from the respective leg stretch unit in the product longitudinal direction, each of the cushioning units has an outer end in the product longitudinal direction, the outer end of each of the cushioning units is provided on an inner side of an end of the front waistline region or the back waistline region in the product longitudinal direction, and each of the cushioning units is a region of the stretchable sheet member of the respective leg stretch unit in which an adhesive is not applied.

9. The disposable diaper according to claim 8, further comprising:

a front waistline retaining unit and a back waistline retaining unit extending along the product widthwise direction in the front waistline region and the back waistline region, respectively, and configured to retain the disposable diaper on a wearer's body, wherein each of the cushioning units overlaps the front waistline retaining unit or the back waistline retaining unit.

10. The disposable diaper according to claim 8, further comprising:

a fastening tape provided in the back waistline region; and a target tape provided in the front waistline region, wherein at least one of the cushioning units overlaps either the fastening tape or the target tape in a thickness direction perpendicular to the product longitudinal direction and the product widthwise direction.

11. The disposable diaper according to claim 8, further comprising:

a fastening tape provided in the back waistline region and having opposing inner and outer ends in the product longitudinal direction; and a target tape provided in the front waistline region and having opposing inner and outer ends in the product longitudinal direction.

12. The disposable diaper according to claim 11, wherein the outer ends of the cushioning units in the back waistline region are arranged between the outer end of the fastening tape and the inner end of the fastening tape in the product longitudinal direction, and the outer ends of the cushioning units in the front waistline region are arranged between the outer end of the target tape and the inner end of the target tape in the product longitudinal direction.

13. The disposable diaper according to claim 8, further comprising a sheet member, wherein each of the leg stretch units is directly attached to the sheet member by an adhesive, and each of the cushioning units is free of direct attachment to the sheet member by the adhesive.

14. The disposable diaper according to claim 13, wherein each of the leg stretch units is a region of the respective stretchable sheet member in which an adhesive is applied.

15. A disposable diaper, comprising:

a front waistline region;

a back waistline region;

a crotch region positioned between the front waistline region and the back waistline region;

a pair of leg hole openings;

an absorber spanning the crotch region and extending to the front waistline region and back waistline region;

a product longitudinal direction from the front waistline region towards the back waistline region;

a product widthwise direction perpendicular to the product longitudinal direction;

a fastening tape provided in the back waistline region;

a target tape provided in the front waistline region;

a pair of leg stretch units formed along the leg hole openings and being stretchable in at least the product longitudinal direction, each of the leg stretch units having a front end and a back end in the product longitudinal direction; and a cushioning unit provided adjacent to each of the ends of each of the leg stretch units in the product longitudinal direction, respectively, wherein each of the leg stretch units is configured from a stretchable sheet member, at least a part of each of the cushioning units has a dimension in the product widthwise direction greater than a width of the respective leg stretch unit in the product widthwise direction, each of the cushioning units is provided on an outer side of the respective leg stretch unit in the product longitudinal direction, and is not provided on an inner side of the respective leg stretch unit in the product widthwise direction, a width of each of the cushioning units in the product widthwise direction gradually increases away from the respective leg stretch unit in the product longitudinal direction, each of the cushioning units has an outer end in the product longitudinal direction, the outer end of each of the cushioning units is provided on an inner side of an end of the front waistline region or the back waistline region in the product longitudinal direction, and at least one of the cushioning units overlaps either the fastening tape or the target tape in a thickness direction perpendicular to the product longitudinal direction and the product widthwise direction.

\* \* \* \* \*